(12) United States Patent
Gunzer et al.

(10) Patent No.: US 6,680,201 B2
(45) Date of Patent: Jan. 20, 2004

(54) AGENT FOR THE REMOVAL OF TURBIDITY IN BIOLOGICAL SAMPLES

(75) Inventors: Gerhard Gunzer, IRL-Ennis (IR); Tracey Larkin, Dooradoyle (IR); Annegret Pfuetzner, Ennis (IR)

(73) Assignee: Olympus Diagnostica GmbH, Hamburg (DE)

( * ) Notice: Subject to any disclaimer, the term of this patent is extended or adjusted under 35 U.S.C. 154(b) by 29 days.

(21) Appl. No.: 10/066,902

(22) Filed: Feb. 4, 2002

(65) Prior Publication Data
US 2002/0151074 A1 Oct. 17, 2002

(30) Foreign Application Priority Data
Feb. 19, 2001 (EP) .............................. 01103991

(51) Int. Cl.[7] .............................. G01N 31/00
(52) U.S. Cl. ............................ 436/17; 436/8; 436/174; 436/175; 252/408.1
(58) Field of Search .................. 436/8, 17, 18, 436/174, 175; 252/408.1

(56) References Cited

U.S. PATENT DOCUMENTS

| | | | | |
|---|---|---|---|---|
| 3,853,465 A | * | 12/1974 | Rush et al. ................. 436/174 |
| 4,184,848 A | * | 1/1980 | Batz et al. ................... 436/175 |
| 4,184,921 A | * | 1/1980 | Roeschlau et al. ............ 435/11 |
| 4,282,001 A | | 8/1981 | Klose et al. |
| 4,503,146 A | * | 3/1985 | Yun et al. ..................... 435/19 |
| 4,626,511 A | * | 12/1986 | Artiss et al. ................... 436/8 |
| 4,649,120 A | * | 3/1987 | Steuer et al. ................. 436/13 |
| 4,708,939 A | | 11/1987 | Siedel et al. |
| 5,258,315 A | * | 11/1993 | Vormbrock ................. 436/174 |
| 5,310,679 A | * | 5/1994 | Artiss et al. ................... 436/18 |

FOREIGN PATENT DOCUMENTS

| | | | |
|---|---|---|---|
| EP | 0 004 857 A3 | | 2/1979 |
| EP | 404590 | * | 12/1990 |
| JP | 10-213582 | * | 8/1998 |

* cited by examiner

*Primary Examiner*—Maureen M. Wallenhorst
(74) *Attorney, Agent, or Firm*—Rankin, Hill, Porter & Clark LLP

(57) ABSTRACT

An Agent for the removal of turbidity and biological samples including 0.5–10 mM Phenol, 0.5–15% polyoxyethylated triglyceride and at least one non-ionic tenside in a range of 0.5–15% capable of dissolving the polyoxyethylated triglyceride.

5 Claims, 1 Drawing Sheet

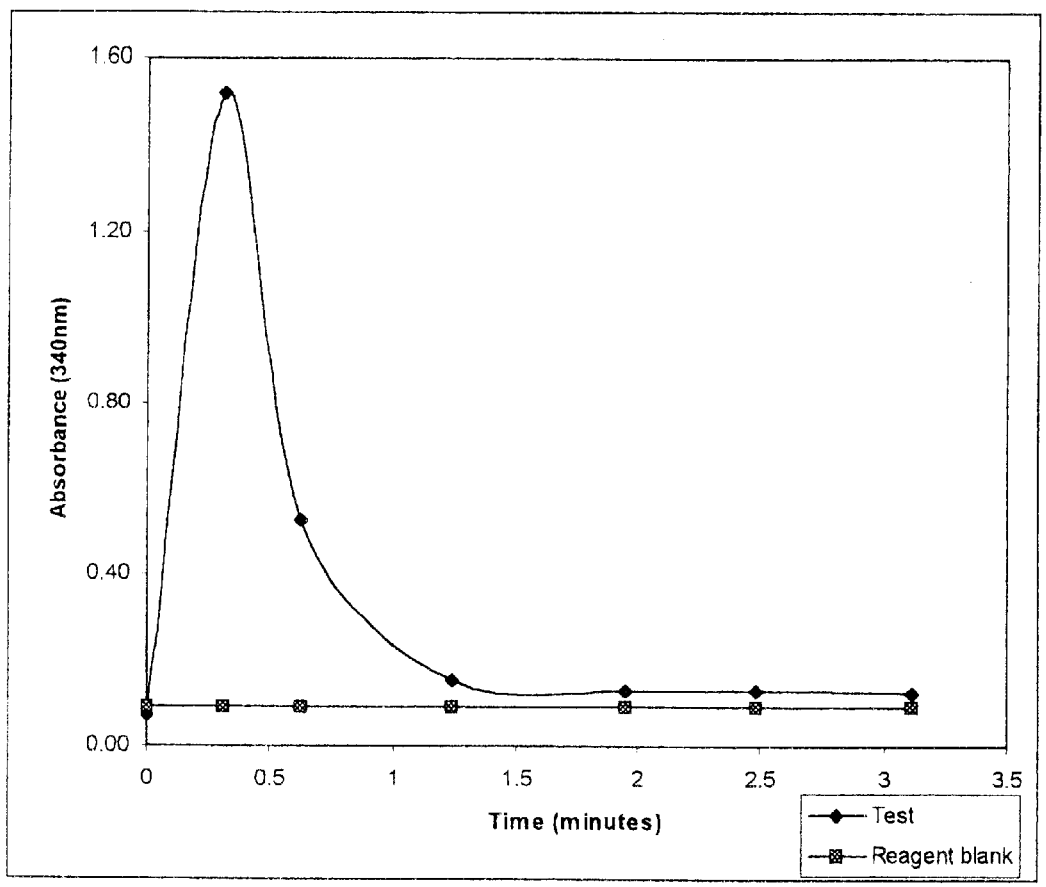
Fig 1 Removal of turbidity from lipemic sample.

AGENT FOR THE REMOVAL OF TURBIDITY IN BIOLOGICAL SAMPLES

FIELD OF THE INVENTION

The present invention relates to an agent for the removal of turbidity in bio-logical samples, particularly serum or plasma samples.

BACKGROUND OF INVENTION

Turbidity typically occurs in plasma or serum samples (lipemic samples) that have an increased content of triglyceride-rich lipoprotein particles, e.g. chylomicrons.

It is particularly necessary to use agents for the removal of turbidity in order to perform photometric analysis of lipemic samples in chemical or clinical diagnosis. If the component to be analysed absorbs at a wavelength corresponding to the absorbing wavelength of the triglycerides causing the turbidity, correct photometric analysis of the component in question will be difficult if not impossible. This applies especially when the concentration of the component to be determined is very low such as, for example, when the analyte is Cell Reactive Protein (CRP).

A common example of a photometric procedure in which the interference of turbidity must be excluded is the assay of CRP. This assay uses anti-human CRP antibodies that specifically react with the CRP in the sample to form insoluble aggregates. The assay is initiated by the addition of the antibodies and the increase in CRP-antibody-aggregates is measured photometrically at 340 nm. The triglycerides in lipemic samples also absorb at this wavelength, so there is a risk of overlapping extinction signals.

To resolve this problem with lipemic samples, several agents are known in the prior art that can be added in order to remove turbidity. In this connection, U.S. Pat. No. 4,708,939 discloses an agent comprising a polyethoxylated triglyceride and a secondary n-alkane sulphonate in an aqueous solution. This known agent requires relatively high detergent concentrations, which can affect certain assays, especially immunoturbidimetric assays. In addition n-alkane sulphonate is an aggressive detergent that can inhibit the reaction of interest. This known agent therefor cannot give total clearing and optimum antibody-antigen reaction.

SUMMARY OF INVENTION

The object of the present invention is to provide an agent for the removal of turbidity that is particularly adapted for use with CRP assays, but can be used also with other assays.

An agent according to the invention comprises 0.5 to 10 mM phenol, 0.5 to 15% of a polyoxyethylated triglyceride, and 0.5 to 15% of at least one further non-ionic tenside. Preferably a combination of two further non-ionic tensides is included.

BRIEF DESCRIPTION OF THE DRAWING

These and further features of the invention will be apparent with reference to the following description and drawing, wherein:

FIG. 1 is a graph of time versus absorbance showing the change in turbidity over time of a mixture of a clearing agent of the present invention and a lipemic sample.

DETAILED DESCRIPTION OF THE INVENTION

In the agent according to the invention, a polyethoxylated triglyceride (triglyceridethoxylate) is necessary to obtain total clearing of the sample. A suitable polyethoxylated triglyceride can have a HLB value in the range of 4–16, preferably 6. The preferred range of concentration is 0.5 to 2%. Preferred polyoxyethylated triglycerides are available under the tradenames MULSIFAN RT 163 (Zschimmer & Schwarz GmbH & Co.) or TAGAT CH-40 (Goldschmidt AG).

The polyoxyethylated triglycerides alone cannot dissolve in the mixture and thus result in a precipitate. In order to obtain dissolution, at least one further non-ionic tenside that assits in the solubilisation of the polyethoxylated triglycerides is required in the sample.

Suitable examples of non-ionic tensides that can be used include: THESIT, TERGITOL, TRITON, BRIJ, NONIDET P-40, and TWEEN 20 (Sigma-Aldrich Ltd.).

The required non-ionic tensides are straight or branched polyoxyethylene ethers with a low degree of oxyethylation (2–10 oxyethylene units per molecule) and 10–18 carbon atoms.

Preferably, the further non-ionic tenside is polyoxyethylene (8) isotridecylether, which is available under the tradename GENAPOL X 080. This non-ionic tenside dissolves in the reaction mixture but alone, but does not have a clearing effect. It is required to solubilise the polyethoxylated triglycerides (as stated above). A preferred range of concentration in which the non-ionic tenside can be used is 0.5 to 2%.

A further preferred non-ionic tenside is polyoxyethylene-10-tridecylether, which can be purchased from Sigma. This tenside also dissolves in the reaction mixture and assists the solubilisation of the polyethoxylated triglycerides. A preferred range of concentration is 0.5 to 2%.

In a preferred embodiment, a combination of polyoxyethylene (8) isotride-cylether and polyoxyethylene-10-tridecylether is provided. Such combination allows a very effective dissolution of the polyoxyethylated triglycerides and thereby improves the clearing action of the agent according to the invention.

Phenol has no dissolving effect on the lipids, but acts synergistically with the tensides to increase their clearing action and removal of turbidity. The presence of phenol helps to reduce the effective concentrations of the tensides needed. In the absence of phenol, higher tenside concentrations would be necessary, which would lead to samples having a too high viscosity.

The components in the agent according to the invention are known substances that are already used in agents for the removal of turbidity known in the prior art.

The use of phenol as a synergistically acting component is known from EP 0 004 857. From EP 0 004 857 it is also known to use GENAPOL as a non-ionic tenside. The use of further non-ionic tensides is known from the U.S. Pat. No. 4,708,939 cited above. However, the prior art discloses the use of only one of the components or sub-combinations thereof. None of these prior art references shows the combination of all of them as in the agent according to the invention.

It surprisingly turned out that all components included in the agent according to the invention are necessary in order to effectively remove turbidity with minimal effects to a possible antibody-antigen reaction. Theoretically, GENAPOL and polyoxyethylene-10-tridecylether together could effectuate clearing. However, the concentrations required for clearing would be so high that any antibody-antigen reaction would be totally inhibited. If according to the invention MULSIFAN and phenol are added, the concentrations of GENAPOL and polyoxyethylene-10-tridecylether can be reduced, which allows clearing without affecting immunological reactions.

In principle the agent according to the invention can be used in all immuno-assay formats where there is a likelihood of interaction of contributing to lipemia.

The example given below uses an immunoturbidimetric format. Those skilled in the art would be aware of associated benefits for other formats including, but not limited to, latex-enhanced assays, magnetic particle chemiluminescent immunoassays, immunofluorescent assays (polarised and non-polarised), ELISA's, immunochromatographic assays, or any assay format requiring reduction of lipemic and/or other associated non-specific binding problems where the beneficial maintenance of antibody binding characteristics is mediated by the combination of reactants in the present invention.

In the first example, a typical formulation of a clearing agent according to the invention to be used in an assay for the detection of CRP is described. Furthermore another example is added showing the removal of turbidity effectuated by an agent according to the invention in lipemic samples.

EXAMPLE 1
Formulation of a Clearing Buffer (R1) for a CRP-assay

| Reagent | Range | Function |
|---|---|---|
| Purified water | | |
| Tris (100 mM)/Liter | 50–300 mM | Buffer |
| NaCl (100 mM)/Liter | 50–150 mM | Assists clarification & reaction. |
| PEG 6000 (2%) (w/w) | 1–3% | Req. for optimisation of reaction rate |
| Phenol (2 Mm) (Liter) | 0.5–10 mM | Lipid clearing component |
| Polyoxyethylene-10-tridecylether (1.0%) (v/v) | 0.5–2% | Lipid clearing component |
| GENAPOL X 80 (1.0%) (v/v) | 0.5–2% | Lipid clearing component |
| MULSIFAN RT 163 (1.1%) (v/v) | 0.5–2% | Lipid clearing component |
| $NaN_3$ | | Anti microbial agent |
| 4M HCl | | pH reagent to 7.5 |
| Gentamicin sulphate soln. | | Stabilizer |

The buffer R1 is adjusted to pH 7.5 (possible range pH 3–9) and is preferably used at a temperature of 37° C. (possible range 15–40° C.).

For the CRP-assay 250µl of R1 are mixed with 18µl of the sample. Then 30µl of an antiserum solution (R2; includes anti CRP antibodies) are added. After mixing of the sample with R1 buffer and R2 antiserum solution, the CRP in the sample reacts specifically with the anti-human CRP antibodies of R2 to yield insoluble aggregates. The absorbance of these aggregates is proportional to the CRP concentration in the sample.

The purpose of the R1 buffer is to dissolve lipids in lipemic samples and to provide optimum conditions for the immunogical reaction.

EXAMPLE 2

Removal of Turbidity in Lipemic Samples

In this test, a clearing buffer (R3) was used with the following formulation:

100 mM Tris buffer adjusted to pH 7.5 with HCl, 100Mm NaCl, 2% Polyoxyethylene glycol 6000, 2 mM Phenol, 1.0% Polyoxyethylene 10-tridecylether, 1.0% Genapol X 80 and 1.0% MULSIFAN RT 163.

In a cuvette 18µl of a strongly lipemic serum was mixed at 37° C. with 250µl of R3. The change of absorbance at 340nm was determined against dependence on time. The results are illustrated graphically in FIG. 1.

The course of the change of absorbance illustrated in FIG. 1 shows that in the case sample/reagent ratio of 18µl : 250µl, a turbidity of about 1.5 is reduced about 1.5 minutes to a cleared level of about absorbance 0.1 in comparison with the reagent blank. Therefore, after 1.5 minutes complete removal of turbidity has been achieved.

What is claimed is:

1. An agent for the removal of turbidity in biological samples comprising:

0.5–10 mM phenol;

0.5–15% by volume polyoxyethylated triglyceride;

0.5–15% by volume polyoxyethylene-10-tridecylether; and 0.5–15% by volume polyoxyethylene (8) isotridecylether.

2. The agent according to claim 1, wherein the concentration of the polyoxyethylene-10-tridecylether is 0.5–2% by volume.

3. The agent of claim 2, wherein the concentration of the polyoxyethylene (8) isotridecylether is 0.5–2% by volume.

4. The agent according to claim 1, wherein the concentration of the polyoxyethylated triglyceride is 0.5–2% by volume.

5. A mixture comprising the agent according to claim 1, a cell reactive protein (CRP) and an anti-human CRP antibody.

* * * * *

UNITED STATES PATENT AND TRADEMARK OFFICE
CERTIFICATE OF CORRECTION

PATENT NO. : 6,680,201 B2
DATED : January 20, 2004
INVENTOR(S) : Gunzer et al.

It is certified that error appears in the above-identified patent and that said Letters Patent is hereby corrected as shown below:

<u>Title page,</u>
Item [57], ABSTRACT,
Line 1, delete "and" and insert -- in --.

Signed and Sealed this

Sixteenth Day of March, 2004

JON W. DUDAS
*Acting Director of the United States Patent and Trademark Office*